(12) United States Patent
Cordeira Da Silva et al.

(10) Patent No.: US 7,732,188 B2
(45) Date of Patent: Jun. 8, 2010

(54) PROTOZOAN STRAINS OF REDUCED VIRULENCE AND USE THEREOF

(75) Inventors: Anabela Cordeira Da Silva, Oporto (PT); Ali Ouaissi, La Boissiere (FR); Denis Sereno, Poussan (FR); Baptiste Vergnes, Montpellier (FR)

(73) Assignees: Institut de Recherche pour le Developpement, Paris (FR); Universidade Do Porto, Oporto (PT)

( * ) Notice: Subject to any disclaimer, the term of this patent is extended or adjusted under 35 U.S.C. 154(b) by 892 days.

(21) Appl. No.: 10/577,560

(22) PCT Filed: Oct. 25, 2004

(86) PCT No.: PCT/FR2004/002735
§ 371 (c)(1),
(2), (4) Date: Sep. 28, 2006

(87) PCT Pub. No.: WO2005/044844
PCT Pub. Date: May 19, 2005

(65) Prior Publication Data
US 2007/0224224 A1    Sep. 27, 2007

(30) Foreign Application Priority Data
Oct. 29, 2003  (FR) .................................. 03 12689

(51) Int. Cl.
*A61K 39/112* (2006.01)
(52) U.S. Cl. ................................. 435/258.3; 424/269.1
(58) Field of Classification Search ........................ None
See application file for complete search history.

(56) References Cited

U.S. PATENT DOCUMENTS 6,248,329 B1 *   6/2001   Chandrashekar et al. . 424/191.1
2002/0177697 A1 *  11/2002   Fasel et al. ................. 536/23.1

OTHER PUBLICATIONS

Ellis, R.W. (Chapter 29 of "Vaccines" [Plotkin, S.A. et al. (eds) published by W. B. Saunders company (Philadelphia) in 1988, especially p. 571, 2nd full paragraph].*

Cordeiro-Da-Silva A et al: "Identification of antibodies to Leishmania silent information regulatory 2 C SIR2 ) protein homologue during canine natural infections: pathological implications." Immunology Letters, (Apr. 3, 2003) 86 (2) 155-62., Apr. 2003, XP001181346, the whole document.

Titus R G et al: "Development of a Safe 1-14 Live Leishmania Vaccine Line by Gene Replacement" Proceedings of the National Academy of Sciences of USA, National Academy of Science. Washington, US, vol. 92, Oct. 1995, pp. 10267-10271, XP002052134, ISSN: 0027-8424 cited in the application, the whole document.

Garcia-Salcedo Jose A et al: "A chromosomal SIR2 homologue with both hi stone NAD-dependent ADP-ri bosyltransferase and deacetyl ase activities is involved in DNA repair in Trypanosoma brucei ." EMBO Journal, (Nov. 3, 2003) 22 (21) 5851-62., Nov. 2003, XP002281455.

Vergnes Baptiste et al: "Cytoplasmic SIR2 homologue overexpression promotes survival of Leishmania parasites by preventing programmed cell death." Gene, (Aug. 21, 2002) 296 (1-2) 139-50., Aug. 2002, XP004386950, cited in the application.

* cited by examiner

Primary Examiner—Patricia A Duffy
(74) Attorney, Agent, or Firm—Young & Thompson

(57) ABSTRACT

The present invention relates to a protozoan strain of the family of the Trypanosomatidae the virulence of which is lower than that of the corresponding wild-type strain, characterized in that at least one copy of the SIR2 gene present in the genome of the strain is inactivated.

2 Claims, 7 Drawing Sheets

SEQUENCE LISTING

<160> NUMBER OF SEQ ID NOS: 6

<210> SEQ ID NO 1
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
gaattcgata tgacagggtc tccg                                           24

<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ctcgagcagt caccatgttg gcag                                           24

<210> SEQ ID NO 3
<211> LENGTH: 1122
<212> TYPE: DNA
<213> ORGANISM: Leishmania infantum

<400> SEQUENCE: 3
atgacagcgt ctccgagagc gccacatcag gagcatgtcc tcggagagcc gaccttggaa    60
gggcttgcgc actacatcag gagaagaat gtgcggcgca ttctcgtgct cgtcggagca    120
ggcgccagtg tagctgccgg catcccagac tttcgctcac ctgacaccgg gatctacgcc   180
aacctcggca agtacaacct cgaagacccg accgatgcct tttcactgac ccttctgcgc   240
gagaagccag agatattcta ctctatcgca cgggagctga acttgtggcc tgggcacttt   300
cagcccaccg cggtacatca cttcatccga ctgttgcaag acgagggccg tctcctgcgc   360
tgctgcacgc agaacattga cggcctggag aaggcagcgg gcgtgtcgcc ggagctcctc   420
gtcgaggcgc atggctcttt cgctgctgcc gcctgcattg aatgccacac accattcagc   480
attgagcaga actacctgga ggcgatgagc ggtacggtct cccgctgctc tacatgcggc   540
ggcattgtga agcccaacgt cgttttcttt ggtgaaaatt tgccggacgc gttcttcgac   600
gcgctgcacc acgacgcccc gatcgcggag ctggtcatca tcatcgggac atcgatgcag   660
gtgcacccgt tcgcgttgct gccgtgcgtc gtgcccaagt cagtcccgcg cgttgtcatg   720
aaccgtgagc gagttggcgg cctcctcttc cgctttcctg atgacccgct caacaccgtc   780
cacgaggatg cggttgccaa ggagggacgc tcgtcctctt cgcagagtcg ttccccgtcc   840
gcgtcgccac ggcgcgagga gggggggaaca gaggacagcc cctcgtcgcc aaacgaggag   900
gtcgaagagg cgtcgacgtc cagctcgagc gacggctacg gcagtacgg tgactaccac     960 gcccacccg atgtctgccg ggatgttctc ttccgcggcg actgccagga gaacgtggtg   1020
acgctggcgg agtacctggg tctgagcgag gcgctggcaa agcgcatgcg cttatccgat   1080
gcagcaccag ctactgcaca gagggcgccg aatgagacgt ga                      1122

<210> SEQ ID NO 4
<211> LENGTH: 1146

-continued

```
<212> TYPE: DNA
<213> ORGANISM: Leishmania major

<400> SEQUENCE: 4
atgacagggt ctccgagagc gccgcatcag gaacatgccc tcggagagcc gactgtggaa     60
gggcttgcgc gctacatcag ggagaaggat gtgcggcgca ttctcgtgct cgtcggagca    120
ggcgccagcg tagctgccgg catcccagac tttcgctcat ctgacaccgg gatctacgcc    180
aagctcggca agtacaacct cgacgacccg accgatgcct tttcgctgac tcttctgcgc    240
gagaagccag agatattcta ctctatcgca cgggagctga acttgtggcc tgggcacttt    300
cagcccaccg cggtgcatca cttcatccga ctgttgcaag acgagggccg tcttctgcgc    360
tgctgcacgc agaacattga tggtctggag aaggcagcgg gcgtgtcgcc ggagctcctg    420
gtcgaggcgc atgggtcttt cgctgccgcc gcctgcatcg aatgccacac gccattcagc    480
attgagcaga actacctgga ggcgatgagc ggcacggtgt cccgctgctc tacatgcggc    540
ggcattgtga agccaaacgt cgttttcttt ggtgaaaatt tgccggacgc gttcttcgac    600
gcgctgcacc acgacgcccc gatcgcggag ctggtcatca tcatcgggac atcgatgcag    660
gtgcacccgt tcgcgttact gccgtgcgtc gtgcccaagt ccatcccgcg cgttctcatg    720
aaccgcgagc gagttggcgg cctcctcttc cgctttcctg atgacccgct cgacaccatc    780
cacgacgatg cggttgccaa ggagggacgc tcgtcctctt cgcagagccg ttccccgtcc    840
gcgtcggcgc ggcgcgagga ggggggacg gaggacggct cctcgtcgcc gaacgaggag    900
gtcgaagacg cgtcgacgtc cagttcgagt gacggctacg gtcagtacgg tgactactac    960
gcccaccccg atgtctgccg ggatgttttc ttccgcggcg actgccagga gaacgtgctg   1020
aagctggccg agtgcctggg cctcagggag gcgctggcca agcgatgcgc ttctccggtg   1080
cggcaccagc tacggcacga aagacgtcga atgagacgtg agtctgaatt gctgccaaca   1140
tggtga                                                              1146

<210> SEQ ID NO 5
<211> LENGTH: 775
<212> TYPE: DNA
<213> ORGANISM: Leishmania amazonensis

<400> SEQUENCE: 5
ccctccaacc tagcaagtac aacctcgacg acccgaccga cgccttttca ctgacccttc     60
tgcgggagag acccgagata ttctactcga tcgcacggga gctgaacttg tggcctgggc    120
actttcagcc caccccggta catcacttca tccgactgtt gcaagatgag ggtcgtctac    180
tgcgctgctg cacgcagaac attgacggcc tggagaaggc cgcgggcgtg tcgccagagc    240
tcctcgtcga ggcacatggg tcttttgctg ccgccgcctg cattgaatgc cacacgccat    300
tcagcattga gcagaactac ctggaggcga tgagcggtac ggtctcccgc tgctctacat    360
gcggcggaat tgtaaaacca aacgttgttt tcttcggtga aaatttgccg gacgctttct    420
tcgacgcgct acaccacgat gccccgatcg cggagctgac tatcatcatc gggacatcga    480
tgcaggtgca cccgttcgcg ctgctgccgt gcgtcgtgcc caagtcagtc ccgcgcgttg    540
tcatgaaccg cgagcgagtt ggtggcctcc tcttccgctt tcctgatgac ccgctgaaca    600
ctgtccacga cgatgcggtt gccaaggagg gtcaatcgtc ttcttcgcag agtcgttccc    660
catccgcgtc ggcgcggtgc gagaagggag gggtagagga cagatcttca tcgccgaagg    720
aggaggtcga cgaagcgtcg acgtccggct cgagcgacgg ctacgggcag tacgg         775
```

```
<210> SEQ ID NO 6
<211> LENGTH: 1056
<212> TYPE: DNA
<213> ORGANISM: Trypanosoma brucei

<400> SEQUENCE: 6
atgacagaac cgaagttagc aaccacgcac gtagtgggtg aacccacctt cgaaggactg      60
gcacggttca ttgagcgaaa caacatcacc aaaatatttg ttatggtggg cgcagggata     120
agcgttgcag ctggaatccc cgacttccgc tctccccaca ccggcttgta cgctaaactc     180
agtcgctaca atctcaactc accggaggac gccttctcac tccctctctt gcgtcaacaa     240
ccaagtgtgt tttacaacat tctgatggat atggacctct ggcccgggaa gtattgtcct     300
acgacggttc accactttat cagtctactc gccaagaagg gcatgttatt atgctgttgt     360
acgcagaaca tagacgggtt ggaacgcgcc tgcggaattc cagagtcttt actagttgaa     420
gcccatggtt ccttctcttc cgcatcatgt gttgactgtc acgcgaaata tgacatcaac     480
atcgcgaggg cggagacaag ggctggaaaa gtgcctcatt gcaatcaatg tggtggtata     540
gtgaaacccg acgtggtttt ctttggcgag aatctcccgg aggcgttttt taacgtagcg     600
ggactcattg aggaaacgga attgctgctt attttgggaa cctcacttca agtccaccca     660
tttgccgacc ttgcgctcat ggtgccctct gacgtgccac gagtgttgtt taacttggag     720
cgtgtgggcg ggaggatgtt ccgctttcct acggaccgaa cacccaattt ccgcgccagt     780
tcctatcgtc tcagcactgg aaatggcaat ggcagtaaaa ttagcagtgg ggacagcagc     840
agcagcagca gcgtcgacgg gtatgaccag tttacgctcg cagagaatga cgagacgggt     900
gtgttgcgtg acattttctt tcctggtgac tgtcaggtgt ctgttcgttc ctttgctcag     960
gcgttgggct tcggagagca gcttgacgcc tctgtacgtg agggaaggga aatatttgag    1020
cgcactcggc gtagggaaaa agtcgttgag ggttaa                              1056
```

PROTOZOAN STRAINS OF REDUCED VIRULENCE AND USE THEREOF

A subject of the present invention is protozoan strains of reduced virulence and use thereof.

The flagellated protozoans of the family of the Trypanosomatidae are responsible for numerous diseases affecting humans and animals.

Thus, among the protozoans of the genus *Trypanosoma, T. brucei* and *T. cruzi* are for example responsible for sleeping sickness and Chagas' disease respectively.

The protozoans of the genus *Leishmania*, such as *L. aethiopica, L. donovani, L. infantum, L. major, L. mexicana* or *L. tropica* are responsible for leishmaniosis. These infections are endemic in more than 88 countries and affect a significant portion of French territory. Around the Mediterranean, and in France in particular, leishmaniosis is essentially caused by *L. infantum*. Worldwide, the WHO estimates the number of individuals infected with parasites at 12 million, and more than 350 million people are exposed daily. Three major forms of leishmaniosis exist, the most severe form of which, visceral leishmaniosis, can prove fatal in the absence of treatment. This situation has been aggravated, since the emergence of HIV, by the fact that these infections are encountered more and more as opportunist diseases in patients suffering from acquired immunodeficiency syndrome (AIDS), in particular in South-Western Europe. The parasite uses its host's depressed immune status in order to become implanted or reactivated.

Current leishmaniosis treatments make use of medicaments which are difficult to handle, such as amphotericin B or medicaments belonging to the family of antimonials, the side effects of which are significant.

To date, no vaccines exist making it possible to prevent *Leishmania* infections. The development of such vaccines is the subject of numerous research programmes. These are concentrated on three main areas; the preparation of killed vaccines, of live attenuated vaccines or of subunitary vaccines. Among these three areas, the preparation of live attenuated vaccines seems be the most promising; this type of vaccine in fact allows an immunization which is closed to that achieved by the wild-type parasite. Moreover, modern molecular biology techniques make it possible to prepare strains of virulence reduced by specific inactivation of certain virulence genes. Several strains of *Leishmania*, a virulence gene of which has been inactivated have thus been prepared (Titus et al. (1995) *Proc. Natl. Acad. Sci. USA*, 92:10267-10271, WO 98/44943, EP 0 716 697, EP 0 806 476). The choice of the gene to be inactivated is crucial as it affects the obtaining of an appropriately attenuated strain, i.e. one with a replicative ability sufficient to stimulate the immune system, but limited in order to avoid any risk of infection, in particular in an immunodepressed subject.

The SIR2 proteins, originally discovered in yeast, are known to be involved in the condensation of chromatin by deacetylation of histones in certain chromosomal regions: the loci HMR and HML responsible for mating-type switching, the subtelomeric regions, and the repetitions of rDNA where SIR2 prevents the formation of extra-chromosomal minicircles by homologous recombination (Guarente et al. (1999) *Nat. Genet.* 23:281-5; Gartenberg et al. (2000) *Curr. Opin. Microbiol.* 3:132-7; Min et al. (2001) *Cell* 105:269-79). Other works have demonstrated its involvement in the DNA repair mechanisms (Tsukamoto et al. (1997) *Nature* 388:900-3).

However the biological role of SIR2 is not restricted to "silencing" and DNA repair, and the most surprising function attributed to SIR2 is certainly that of increasing the longevity of organisms possessing an additional copy of this gene. This has been demonstrated in yeast and *Caenorhabditis elegans* (Guarente et al. (2000) *Genes Dev.* 14:1021-6; Tissenbaum et al. (2001) *Nature* 410:227-30).

Systematic sequencing programmes have made it possible to characterize other proteins related to SIR2 in different eukaryotic and prokaryotic organisms. From now on, reference will be made to the protein family comprising the actual nuclear SIR2 proteins and the homologues of SIR2 indiscriminately called "Hst" for "Homologue of SIR Two" or "sirtuin" (Frye et al. (2000) *Biochem. Biophys. Res. Commun.* 273:793-8). The biological significance of this diversity of the SIR2 proteins is not yet clearly established, but different works show that all the Hst's studied possess, in the same way as SIR2, a histone deacetylase type enzyme activity which is strictly dependent on NAD. This characteristic has made it possible to bring together the SIR2 proteins in a novel class of histone deacetylase known as class III as opposed to classes I and II which have already been characterized.

The existence of SIR2 homologues having strictly cytoplasmic locations, and the presence of Hst in the prokaryotes which possess no histones, suggests however that these enzymes possess physiological substrates other than histones and therefore other biological functions. The recent works published in this field effectively show an increasing number of "targets" characterized by SIR2 or its homologues. SIRT1 in humans and its murine homologue are thus capable of binding specifically to p53 and inactivating it by deacetylation (Vaziri et al. (2001) *Cell* 107:149-59; Luo et al. (2001) *Cell* 107:137-48). SIRT1, by this means, prevents the entry into apoptosis of cells subjected to stress. The transcription factor TAF168 in mice (Muth et al. (2001) *Embo J.* 20:1353-62), the protein Alba in the archaeobacterium *S. solfataricus* (Bell et al. (2002) *Science* 296:148-51) or more recently the proto-oncogene BCL6 in humans (Bereshchenko et al. (2002) *Nat. Genet.* 32:606-13) are all deacetylated by SIR2 or its homologues. This diversity of partners without direct interrelation and the number of biological processes in which they are involved indicate the significance of this protein family within the cell.

The SIR2 gene of *Leishmania major* (LmSIR2) encoding a protein having a strong sequence homology with SIR2 of yeast has been characterized for the first time by Dr. Ali Ouaissi and his team in 1996 (Yahiaoui et al. (1996) *Gene* 169:115-8). Homologues of this protein have been demonstrated by Western blot in all the other species of *Leishmania* studied (*L. infantum, L. mexicana, L. braziliensis*) as well as in *Trypanosoma cruzi* (Zemzoumi et al. (1998) *Biol. Cell.* 90:239-45). This protein has a heterogeneous cytoplasmic location according to the stage of development and according to the species. It is found associated with cytoplasmic granules in the promastigote forms and has a diffuse cytoplasmic location in the amastigote. The recombinant protein is also capable of binding to the surface of the J774 macrophages and being internalized.

In order to know the biological role of this protein in the parasite, the overexpression of the LmSIR2 protein and of its homologue, the LiSIR2 protein, was carried out in *L. infantum*. The results obtained demonstrate that the expression of these two proteins extends the life of the parasites in stationary phase; this phenomenon being correlated with a prevention of the entry into apoptosis of the parasites (Vergnes et al. (2002) *Gene* 296:139-50).

A subject of the present invention is providing a novel protozoan strain of the family of the Trypanosomatidae, in particular of the genus *Leishmania*, of virulence reduced by the inactivation of a gene the virulence character of which has been recently demonstrated, said strain being more effective in inducing immunity to protozoan infections than certain strains known to date.

A subject of the present invention is also the use of this strain for the preparation of medicaments, in particular vaccines, intended to prevent or treat protozoan diseases.

The present invention relates to a protozoan strain of the family of the Trypanosomatidae the virulence of which is lower than that of the corresponding wild-type strain, characterized in that at least one copy of the SIR2 gene present in the genome of said strain is inactivated.

The virulence of a protozoan strain can be measured by methods well known to a person skilled in the art and in particular as described in Examples 2 and 3 below. In particular, it is possible to measure the parasitic charge over time of a model animal, such as a mouse, infected with a protozoan strain the virulence of which is to be evaluated and compared with that of a similar model animal infected with the corresponding wild-type strain. The strain the virulence of which is to be evaluated is referred to as having lower, or reduced, virulence if the parasitic charge of this strain diminishes more rapidly over time than that of the corresponding wild-type strain.

The inactivation of a gene can be achieved according to different methods well known to a person skilled in the art and in particular as described in Example 1 of the present description. In particular, it is possible to replace, by homologous recombination, the chromosomal sequence of a gene produced by an identical sequence into which the gene sequence for resistance to a selected drug, such as an antibiotic, has been inserted. Alternatively, it is possible to replace all or part of the chromosomal sequence of a given gene, with the gene sequence for resistance to a selected drug, such as an antibiotic, by homologous recombination at the ends.

The identification of an SIR2 gene for a species of the family of the Trypanosomatidae for which it has not yet been identified can be carried out according to techniques well known to a person skilled in the art, starting with the already known sequences of SIR2 of different species, and in particular those of *Leishmania infantum* (GenBank AF487351, SEQ ID NO: 3), *Leishmania amazonensis* (GenBank AF534109, SEQ ID NO: 5), *Leishmania major* (GenBank L40331, SEQ ID NO: 4) and *Trypanosoma brucei* (GenBank AF102869, SEQ ID NO: 6). If the complete or partial sequence of the genome of the strain for which the SIR2 gene is to be identified is available, it is possible to use a BLAST-type sequence comparison program (Altschul et al. (1990) *J. Mol. Biol.* 215:403-410) which makes it possible to detect the sequences exhibiting a sufficient sequence similarity to the already known sequences of SIR2. Alternatively, as described in Example 1 of the present description, it is also possible to produce probes, for example by PCR, from the SIR2 sequences already known, label them using a fluorescent or radioactive label for example, and to carry out screening, for example according to the Southern method, of a complementary or chromosomal DNA bank of a strain for which an SIR2 gene is to be identified.

According to a particular embodiment, said strain is characterized in that a single copy of the SIR2 gene is inactivated.

The genome of the protozoans is diploid, i.e. each gene is present in two copies present on each of the homologous chromosomes respectively.

The use of such a strain is advantageous to the extent that the inactivation of a single copy of the SIR2 gene is sufficient to induce a diminution of the virulence of the strain for which this gene has been inactivated.

According to another advantageous embodiment, the two copies of the SIR2 gene are inactivated.

According to another preferred embodiment, said strain belongs to the genus *Trypanosoma* or to the genus *Leishmania*.

According to yet another preferred embodiment, said strain belongs to the genus *Leishmania* and in particular to the species chosen from the group comprising *L. donovani*, *L. major*, *L. tropica*, *L. mexicana*, *L. infantum*, *L. amazonensis* and *L. braziliensis*.

According to a particularly preferred embodiment, said strain belongs to the species *Leishmania infantum*.

The present invention also relates to an immunogenic composition characterized in that it comprises a strain as defined above.

The present invention also relates to a pharmaceutical composition, in particular vaccinal, comprising as active ingredient a strain as defined above in combination with a pharmaceutically acceptable vehicle.

According to a particular embodiment, said pharmaceutical composition, in particular vaccinal, moreover comprises an adjuvant, such as a strain of *Mycobacterium vaccae* or BCG, alum, monophosphorylated lipid A, or interleukin-12.

The use of adjuvant is well known to a person skilled in the art. The adjuvant compounds make it possible in particular to increase the immune response of the organism to which an immunogenic, pharmaceutical or vaccinal composition is administered, to the immunogenic compound included in said composition.

*Mycobacterium vaccae* or BCG, are live bacterial agents, well known to a person skilled in the art, capable of inducing an activation of the immune system and improving the immune response to the protozoans of the invention.

The other above-mentioned adjuvants are in particular described in "Report on the fourth TDR/IDRI Meeting on Second-Generation Vaccines against Leishmaniasis" of Dumonteil et al., available from the WHO and in Hadman (2002) *Clin. Microbiol. Rev.* 14:229-43.

According to another particular embodiment, said pharmaceutical composition, in particular vaccinal, is suitable for the administration of a single dose of approximately $5.10^4$ to approximately $5.10^7$ protozoans per kg.

The expression "per kg" refers to the body mass of the subject to be treated.

According to yet another particular embodiment, said pharmaceutical composition, in particular vaccinal, comprises as active ingredient a strain of *Leishmania infantum* for which a copy of the SIR2 gene has been inactivated, as defined above.

According to a preferred embodiment, said pharmaceutical composition, in particular vaccinal, also comprises one or more compounds which can be used for the prevention and/or treatment of the diseases linked to a protozoan infection, such as the diseases caused by trypanosomes and leishmaniae, such as:

miltefosine, antimonials, amphotericin B, benznidazole, nifurtimox, pentamidine and its derivatives, arsenic derivatives, melarsopol and difluoromethylornithine, protozoans, in particular of the genus *Trypanosoma* or *Leishmania*, inactivated or of virulence reduced by inactivation of a gene different from SIR2, protozoan antigens, such as the proteins gp46, gp63, LACK, TSA, STI1, Hsp80, SLA, FPA, 1G6, 4H6, GBP, CPA, CPB, LeIF, A2 or lipophosphoglycan, or nucleic acid sequences encoding said protozoan protein antigens.

The diseases caused by trypanosomes correspond in particular to sleeping sickness (*T. brucei*) and Chagas' disease (*T. cruzi*).

Leishmaniosis can in particular be caused by *L. donovani, L. major, L. tropica, L. mexicana, L. infantum, L. amazonensis* or *L. braziliensis*, and manifests itself in four main forms: visceral leishmaniosis (kala azar), cutaneous leishmaniosis, mucocutaneous leishmaniosis, and diffuse cutaneous leishmaniosis.

Advantageously the addition of one or more above-mentioned compounds makes it possible to activate the immune system of the organism to which said composition has been administered in synergistic fashion with the protozoan strains of the invention.

The so-called inactivated protozoans correspond to protozoans killed in particular by autoclaving.

The protozoans referred to as of virulence reduced by inactivation of a gene different from SIR2, correspond in particular to protozoans, in particular *Leishmania*, for which one of the genes DHFR-TS, CPA, CPB, A2, or TR has been inactivated.

The above-mentioned protozoan antigens correspond in particular to antigens of *Leishmania* and are in particular described in "*Report on the fourth TDR/IDRI Meeting on Second-Generation Vaccines against Leishmaniasis*" by Dumonteil et al., available from the WHO, and in Handman (2002) *Clin. Microbiol. Rev.* 14:229-43.

The invention also relates to a product comprising:
at least one strain as defined above,
and at least one compound which can be used for the prevention or treatment of diseases linked to a protozoan infection, such as diseases caused by trypanosomes and leishmaniae, such as:
   miltefosine, antimonials, amphotericin B, benznidazole, nifurtimox, pentamidine and its derivatives, arsenic derivatives, melarsopol or difluoromethylornithine,
   protozoans, in particular of the genus *Trypanosoma* or *Leishmania*, inactivated or of virulence reduced by inactivation of a gene different from SIR2,
   protozoan antigens, such as the proteins gp46, gp63, LACK, TSA, STI1, Hsp80, SLA, FPA, 1G6, 4H6, GBP, CPA, CPB, LeIF, A2 or lipophosphoglycan, or
   sequences of nucleic acids encoding said protozoan protein antigens;

as a combination product for simultaneous or separate use or use spread out over time for the prevention and/or treatment of the diseases linked to a protozoan infection, such as the diseases caused by trypanosomes and leishmaniae.

The invention also relates to the use of a strain as defined above, for the preparation of a medicament, in particular a vaccine, intended for the prevention and/or treatment of diseases linked to a protozoan infection, such as the diseases caused by trypanosomes and leishmaniae.

The invention also relates to the above-mentioned use of a strain of *Leishmania infantum* for which a copy of the SIR2 gene has been inactivated, as defined above, for the preparation of a medicament, in particular a vaccine, intended for the prevention and/or treatment of leishmaniosis, in particular of leishmaniosis caused by *Leishmania infantum*.

Moreover, a particular embodiment of the invention also envisages the use of a strain as defined above, said strain moreover being killed, in particular by thermal or chemical treatment, using glutaraldehyde for example, for the preparation of medicaments or vaccines, in particular within the framework of the prevention and/or treatment of diseases linked to a protozoan infection, such as diseases caused by trypanosomes and leishmaniae.

The invention also relates to the pharmaceutical compositions comprising such killed strains, in combination with a pharmaceutically acceptable vehicle.

DESCRIPTION OF THE FIGURES

FIGS. 1A and 1B represent the loci of the wild-type alleles (LiSIR2) (FIG. 1A) or inactivated by the neomycin resistance genes (LiSIR2::NEO) (FIG. 1B). The restriction sites are represented by H: Hind III, P: Pst I, C: Cla I, S: Sac I. The arrows indicate the size of the restriction fragments obtained.

FIG. 2A represents an analysis according to the Southern transfer method of the genomic DNA originating from wild-type clones of *L. infantum* digested by Pst I (track 1), clones for which a copy of the LiSIR2 gene has been inactivated (tracks 2 and 3) and hybridized with the LiSIR2 probe.

FIG. 2B represents a Southern Blot analysis of the genomic DNA of wild-type clones of *L. infantum* digested by Sac I (track 1), clones for which a copy of the LiSIR2 gene has been inactivated (track 2 and 3), and hybridized with the NEO probe.

FIGS. 3A and 3B represent the growth kinetics of the parasites in the promastigote (FIG. 3A) and amastigote forms (FIG. 3B) of the different clones: wild-type (black squares) and LiSIR2/LiSIR2::NEO (circles and white triangles) inoculated with $2.10^6$ parasites/ml. The x-axis represents time (in days) and the y-axis the number of parasites per ml (to be multiplied by log $10^4$ for FIG. 3A and by $10^4$ for FIG. 3B).

FIGS. 4A and 4B represent the effect of the monoclonal antibody IIIG4 directed against the SIR2 protein of *L. major* on the growth of the amastigotes of wild-type *L. infantum* (FIG. 4A) or for which a copy of the LiSIR2 gene has been inactivated (FIG. 4B). In FIG. 4A the curve with the black triangles represents the effect of IIIG4 diluted 1/20 and the curve with the black squares the effect of the control antibody IIIB9F10 directed against a flagellate protein of *T. cruzi* (Tc24). In FIG. 4B, the curves with the white circles, the white squares, the black circles and the black squares respectively represent the effect of IIIG4 diluted 1/20, IIIB9F10, IIIG4 diluted 1/40 and a control.

FIG. 5A represents the variation compared with the wild-type parasites (as a percentage, y-axis) of the quantity of parasites in G0/G1 phase (1), in S phase (2) or in G2/M phase (3) for parasites overexpressing the SIR2 protein of *L. major* (white column), or having a copy of the inactivated SIR2 gene (LiSIR2/LiSIR2::NEO) (black column).

FIG. 5B represents the percentage of parasites in apoptosis for wild-type parasites (1), having a copy of the inactivated SIR2 gene (LiSIR2/LiSIR2::NEO) (2) or overexpressing the SIR2 protein of *L. major* (3), in the presence of 25 µg/ml Sirtinol (an inhibitor of SIR2) and YOPRO-1 (an apoptosis stain, Idzioreck et al. (1995) *J. Immunol. Methods* 185:249-258).

FIG. 6A represents the reduction of the incorporation of tritiated uracile (y-axis, as a percentage) in macrophages derived from the TPH1 line infected with independent mutant strains of the type LiSIR2/LiSIR2::NEO (white and black columns) compared with macrophages infected with a wild-type strain.

FIG. 6B represents the parasitic charge in the spleens of infected BALB/c mice (y-axis, log of the number of parasites per gram) either by a wild-type strain of L. infantum (black diamonds) or with a strain of L. infantum for which a copy of the SIR2 gene has been inactivated (LiSIR2+/− white squares), as a function of time (x-axis, in weeks), a progressive reduction is observed in the parasitic charge in the mice infected with the mutant clones and no live parasite could be detected 6 weeks after infection.

Figure 7:
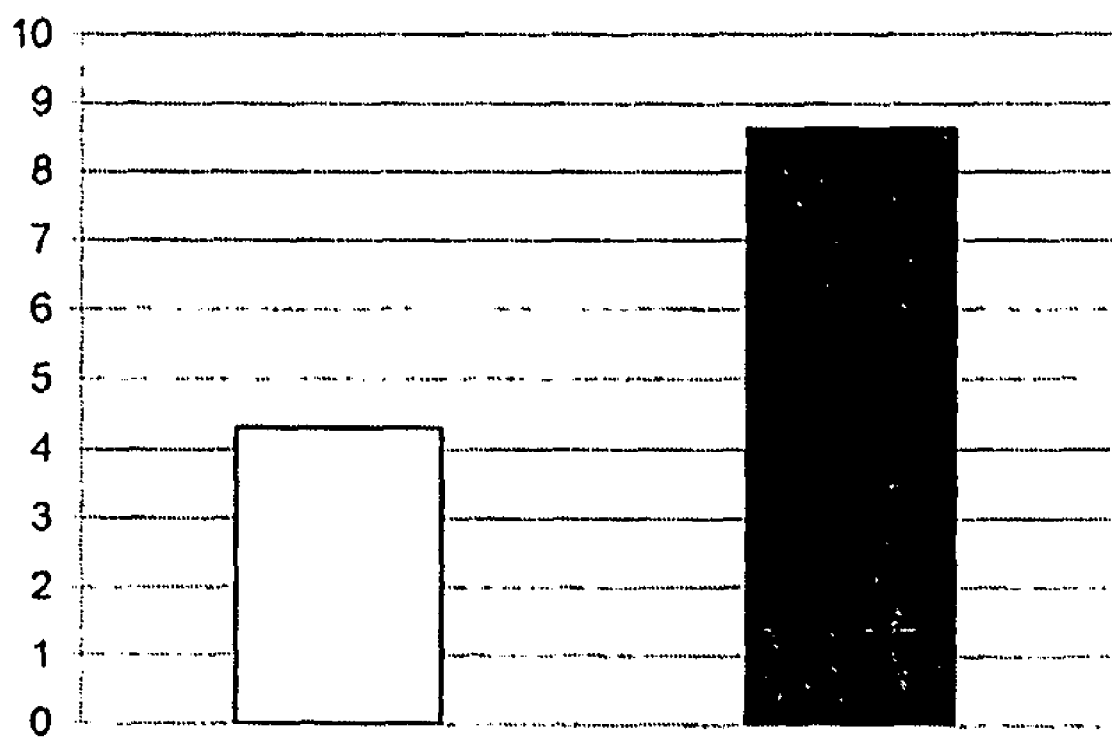
FIG. 7

The FIG. 7 represents the parasitic charge in the spleens of BALB/c mice (y-axis, log of the number of parasites per gram) infected either with a wild-type strain of L. infantum (black bar) or with a strain of L. infantum for which a copy of the SIR2 gene has been inactivated (LiSIR2+/− white bar), then reinfected after 6 weeks with a wild-type strain of L. infantum. The parasitic charge is determined 6 weeks after the reinfection. A significant reduction is observed in the parasitic charge in the mice having been primo-infected with the mutant clones.

EXAMPLES

The present invention results from the demonstration by the inventors of the virulent character of the SIR2 gene in the protozoans of the family of Trypanosomatidae.

Example 1

Obtaining a Strain of *Leishmania infantum* for which the SIR2 Gene is Inactivated 1. Inactivation of the SIR2 Gene of *L. infantum* (LiSIR2)

The single gene LiSIR2 was inactivated in the parasite by homologous recombination.

The promastigote strains of *L. infantum* (clone MHOM/67/ITMAP-263) and the mutant clones derived from it were obtained by limit dilution and cultured at 26° C. in an SDM-79 medium (Brun et al. (1979) *Acta Trop.* 36:289-292) supplemented with 10% foetal calf serum inactivated at 56° C., 100 U/ml of penicillin and 100 μg/ml streptomycin and 10 μg/ml of neomycin (G418) for the period of selection of the recombinant clones. The clonal populations of axenic amastigotes were maintained at 36+/−1° C. in the presence of 5% $CO_2$ in a MAA/20 acellular medium (Sereno et al. (1997) *Antimicrob. Agents Chemother.* 41:972-976).

A genomic DNA bank of *L. infantum* was screened with the probe carrying the SIR2 gene sequence of *L. major* in order to isolate a large genomic fragment containing the LiSIR2 gene and its flanking regions.

Figure 1A:
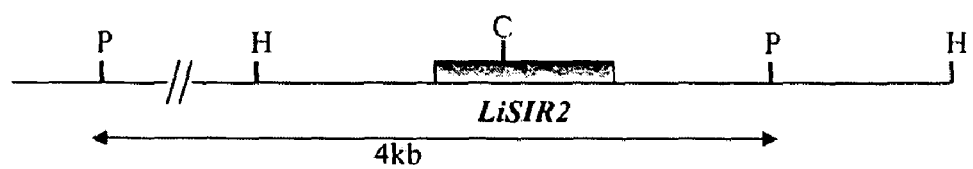
FIG. 1A, FIG. 1B
Figure 1B:
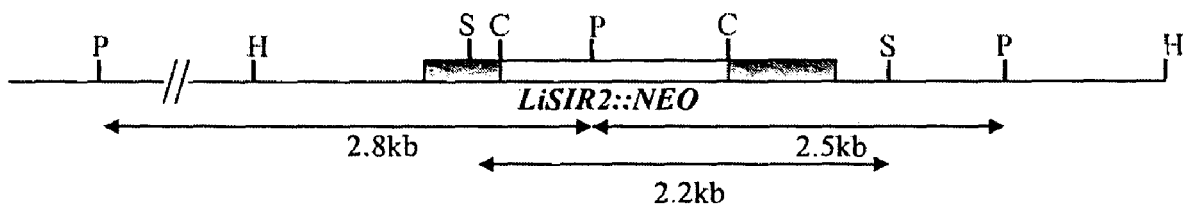

Briefly, the SIR2 gene of *L. major* (Yahiaoui et al. (1996) *Gene* 169:115-8) was amplified by PCR using two specific primers LmSIR2-A (5'-gaattcGATATGACAGGGTCTCCG-3') (SEQ ID NO: 1) and LmSIR2-B (5'-ctcgagCAGTCAC-CATGTTGGCAG-3') (SEQ ID NO: 2). The amplified fragment of 1200 pb obtained was cloned into the vector pCR2.1 using the commercial "TA cloning kit" (Invitrogen). The fragment radiolabelled with α($^{32}$P)dCTP was used to screen the genomic bank of *L. infantum* using standard protocols (Yahiaoui et al. (1996) *Gene* 169:115-8) well known to a person skilled in the art. Positive clones were analyzed by restriction enzymes and analyzed according to the Southern transfer method using the same radiolabelled probe. A fragment of 6 kb generated by the enzyme Hind III carrying the LiSIR2 gene was sub-cloned into the plasmid pUC18 (designation: pUC-SIR) and sequenced. The determination of the reading frames made it possible to identify a nucleotide sequence of 1119 pb (SEQ ID NO: 3) encoding a protein of 373 aa exhibiting 93% identity with the LmSIR2 gene of *L. major*. This sequence was submitted to GenBank under the code AF487351. A diagrammatic representation of the wild-type allele carrying the fragment of 6 kb is given in FIG. 1A. The plasmid pUC-SIR was opened by the enzyme Cla I having a single site in the LiSIR2 gene and treated successively by mung bean nuclease and phosphatase in order to generate dephosphorylated blunt ends. The cassette containing the gene encoding the neomycin phosphotransferase (NEO) used for the construction of the vector for the inactivation was derived from the construction pSPYneo (Papadopoulou et al. (1994) *J. Biol. Chem.* 269:7310-7315). The cassette NEO under the control of the regions rich in pyrimidic bases was isolated by digestion by Bam HI-Bgl II and treated with Klenow polymerase in order to generate blunt ends. The neomycin resistance gene was then integrated into the single Cla I site present in the sequence encoding LiSIR2 (FIG. 1B). The construction linearized with Hind III was then electroporated with the promastigotes of the logarithmic growth phase of the wild-type clone *L. infantum* MON1 (clone: MHOM/67/ITMAP-263). After selection, the transforming parasites were cloned by limit dilution and characterized.

Briefly, the promastigotes were transfected by electroporation with 1 μg of purified linearized DNA on agarose gel as described previously (450 V.cm$^{-1}$ 450 μF) (Vergnes et al. (2002) *Gene* 296:139-50). In a first phase the electroporated promastigotes were incubated in 5 ml of SDM-79 medium without the addition of selected antibiotic for 24 hours. After this stage, the antibiotic neomycin (G418) was added to the culture medium at a rate of 10 μg/ml over two weeks. The parasites obtained were cloned by the limit dilution method in the presence of 10 μg/ml of G418.

2. Molecular Characterization of the LiSIR2+/− Mutants

Figure 2A:
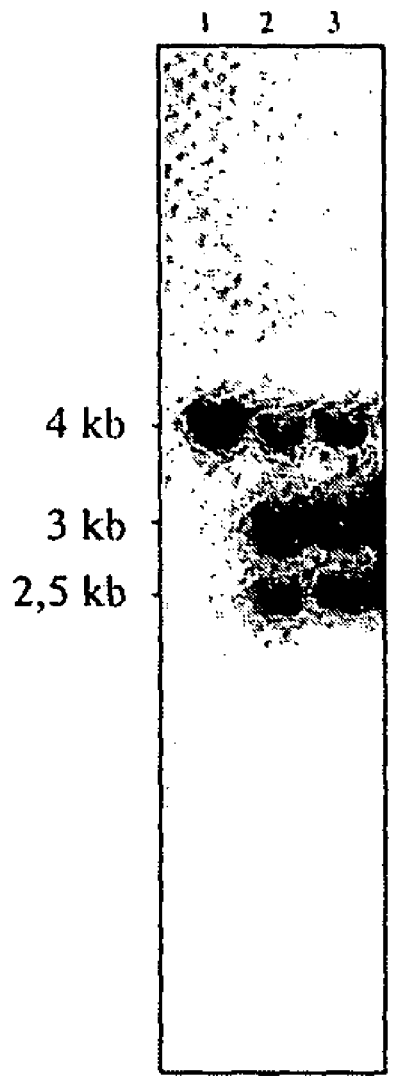
FIG. 2A, FIG. 2B
Figure 2B:
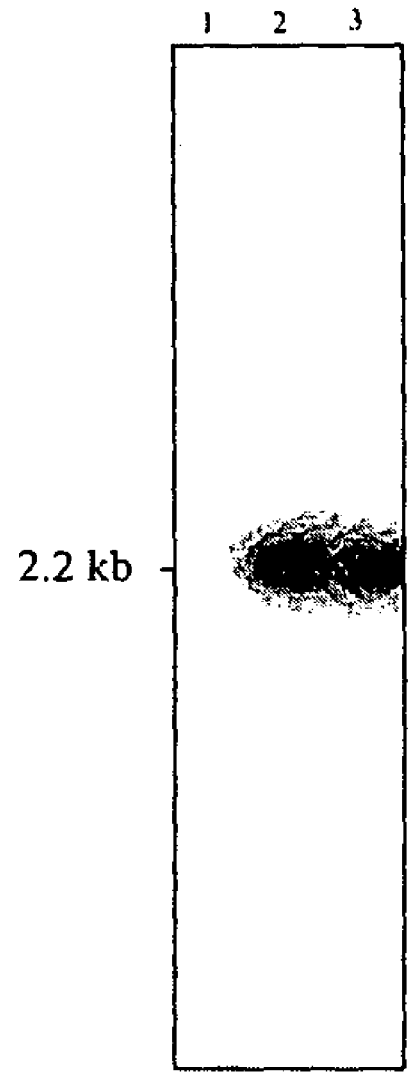

The inactivation of an allele of the LiSIR2 gene was carried out by integrating the construction containing the neomycin resistance gene (mutant LiSIR2+/− or LiSIR2/LiSIR2::NEO). Southern blot reveals in all the recombinant clones the presence of a wild-type allele of 4 kb and two additional fragments of 2.8 kb and 2.5 kb corresponding to the allele LiSIR2::NEO, in accordance with the restriction profile obtained by Pst I (FIGS. 1A, 1B and 2A).

Figure 3A:
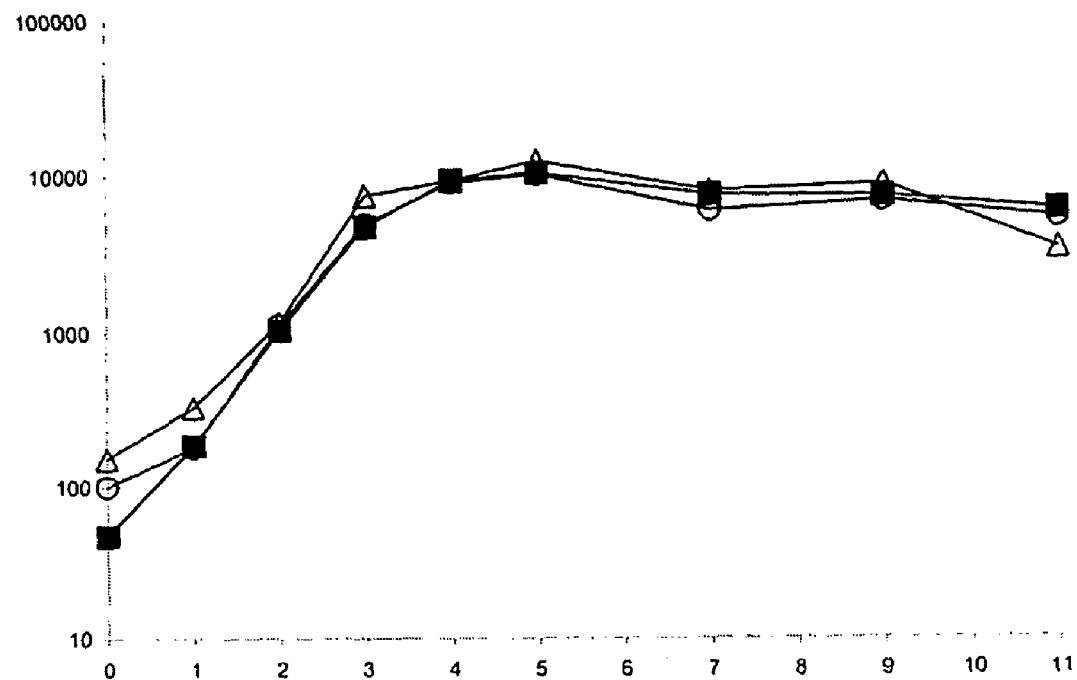
FIG. 3A and FIG. 3B
Figure 3B:
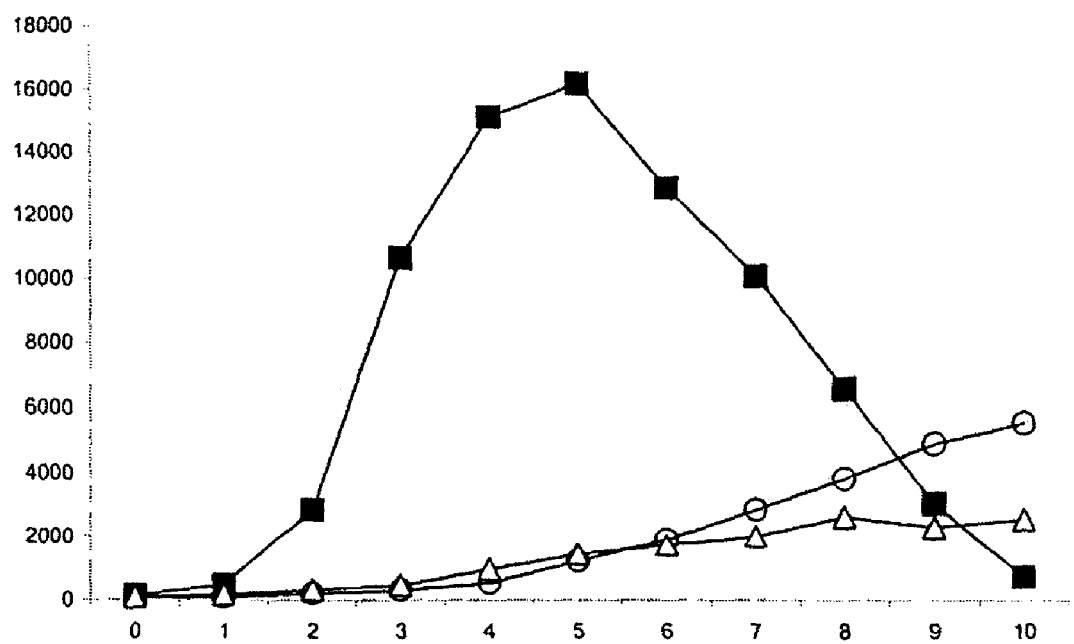

3. Phenotypic Characterization of the LiSIR2+/− Mutant Parasites a. LiSIR2 is Essential for the Multiplication of the Axenic Amastigote Forms In order to study the effect of the inactivation of an allele of the LiSIR2 gene on the proliferation of the parasites in axenic culture, the Inventors produced growth kinetics on the two parasite stages using propidium iodide as a viability marker. The growth curves of the wild-type clone and of the mutants were produced by inoculating the culture medium SDM-79 or MAA/20 with $2.10^6$ or $4.10^6$ promastigotes or amastigotes respectively; the counts were carried out at intervals of 24 hours as described previously (Vergnes et al. (2002) *Gene* 296:139-50). The inactivation of an allele of the LiSIR2 gene does not affect the growth of the parasites in the promastigote form (FIG. 3A). By contrast, in these same parasites in the amastigote form, a strong reduction is observed in their ability to proliferate in culture compared with the wild-type parasites (FIG. 3B).

Figure 4A:
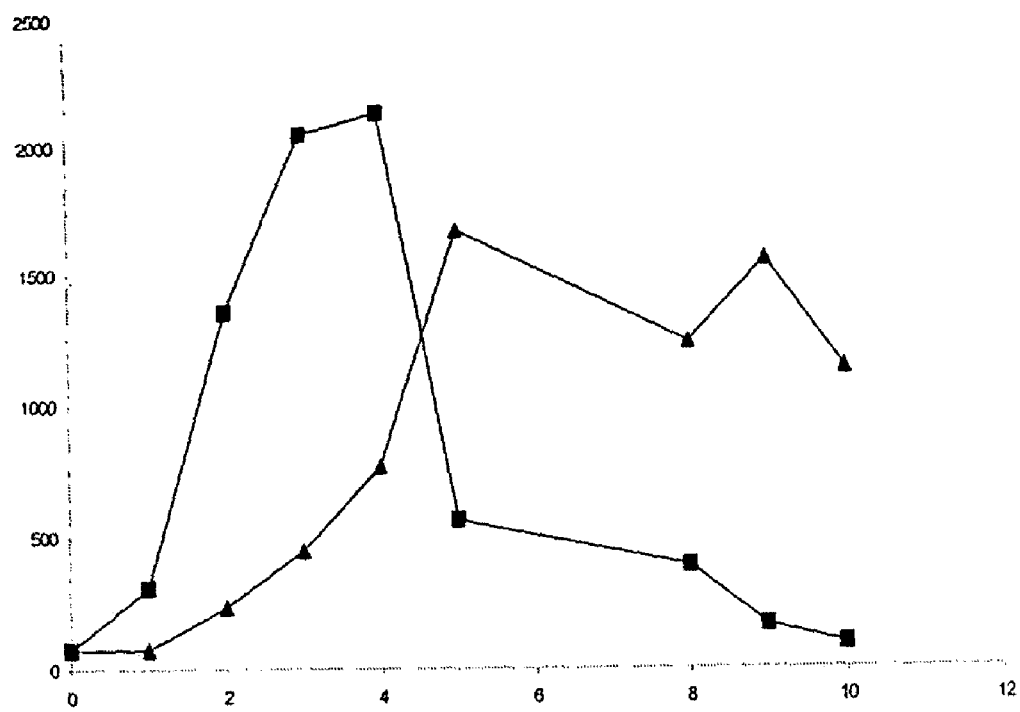
FIG. 4A and FIG. 4B
Figure 4B:
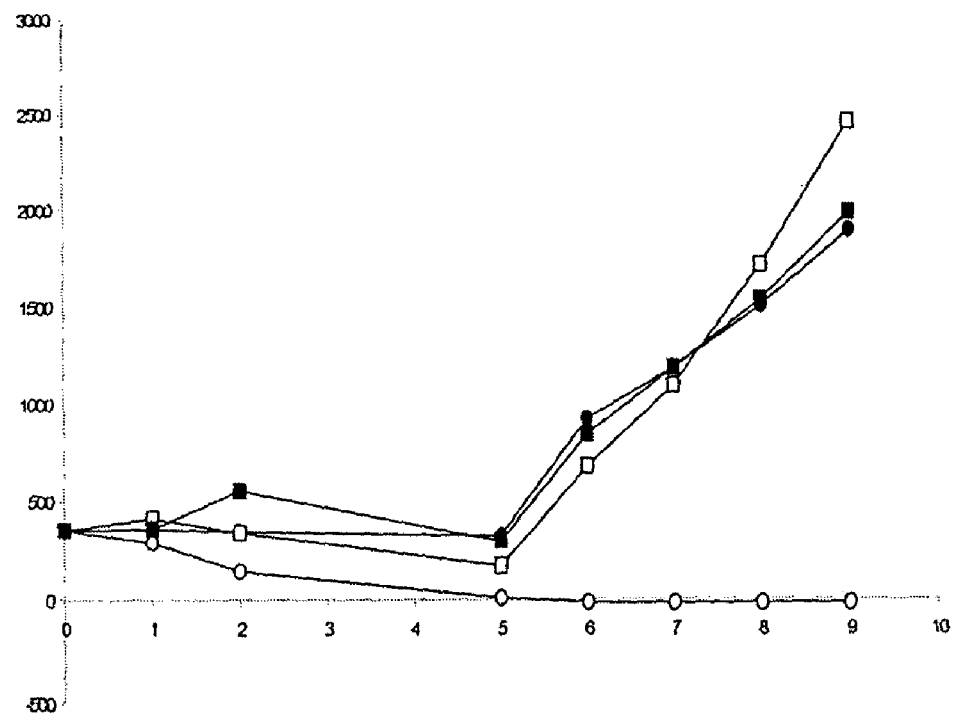
Figure 5A:
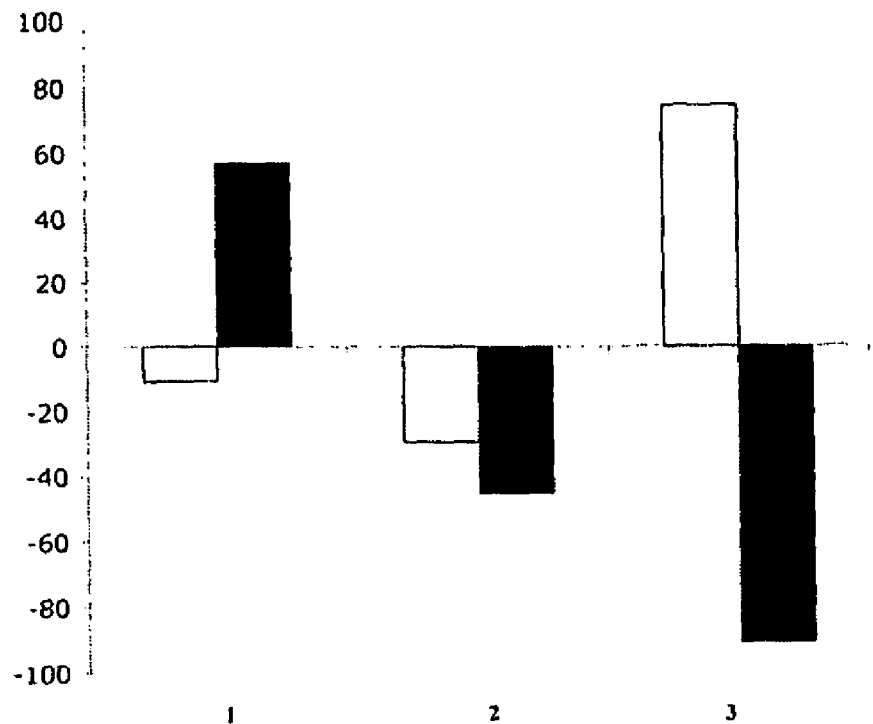
FIGS. 5A and 5B

In order to confirm the direct involvement of the level of synthesis of LiSIR2 in the proliferation capacity of the parasites in the amastigote form, growth kinetics of wild-type amastigotes (FIG. 4A) or amastigotes having lost a copy of the LiSIR2 gene (FIG. 4B) were produced in the presence of the monoclonal antibody IIIG4 (Vergnes et al. (2002) *Gene* 296:139-50) directed against the LmSIR2 protein. A monoclonal antibody IIIB9F10 (Ouaissi et al. (1992) *Biol. Cell.* 75:11-17) of the same isotype directed against the Tc24 protein of *Trypanosoma cruzi* was used as a control. The addition of the antibody IIIG4 to the ¹/₂₀ dilution considerably slows the growth of the wild-type parasites, with the appearance of a very prolonged latency phase. The same parasites in the presence of IIIB9F10 at an identical concentration have a growth kinetic comparable to that of the wild-type clone (FIG. 4A). The same experiment carried out with a parasite clone without a copy of the LiSIR2 gene (LiSIR2+/− clone) shows that the IIIG4 antibody used with the ¹/₂₀ totally blocks the proliferation and kills the parasites. The same antibody diluted to ¹/₄₀ or IIIB9F10 diluted to ¹/₂₀ does not modify the growth kinetics of the amastigotes compared with the LiSIR2+/− control clone. The action of the IIIG4 therefore seems to be dose-dependent which suggests that the LiSIR2 protein is essential for the amastigotes to multiply.

b. The Inactivation of an Allele of the LiSIR2 Gene Blocks the Parasites in G0/G1 Phase of the Cell Cycle In order to know the function of LiSIR2 in the amastigote forms, cell cycle studies were carried out on the mutant parasites having different levels of expression of the LiSIR2 protein compared with the wild-type parasites. The inactivated LiSIR2/LiSIR2::NEO clones possess a strong percentage of cells blocked in the G0/G1 phase of the cycle (FIG. 5A). On the other hand, an enrichment of the cells in the G2/M phase in the parasites overexpressing the LmSIR2 protein (pTEX-LmSIR2 clone) is observed.

Figure 5B:
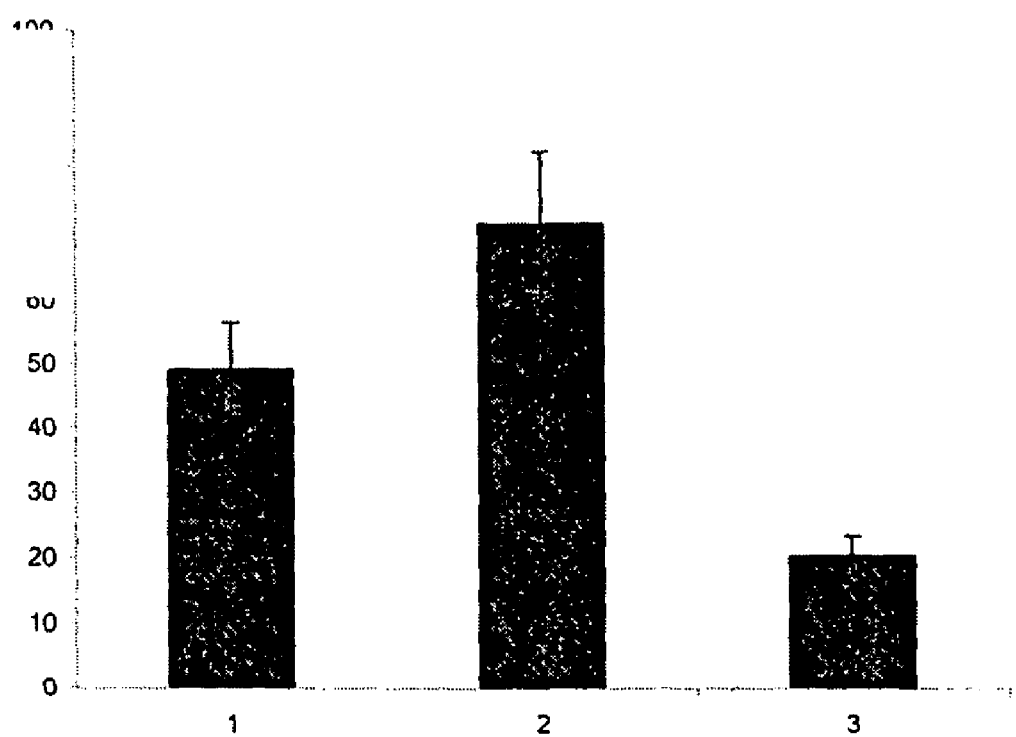

Other experiments were carried out using Sirtinol (Calbiochem) which is a specific inhibitor of the SIR2 proteins. At a concentration of 25 µg/ml an enrichment of the parasites in the G0/G1 phase is observed with the appearance in clone 2 of a pre-G0/G1 peak which corresponds to the fragmentation of the genomic DNA observed during the final apoptosis phase. The wild-type and overexpressing clones have respectively intermediate phenotypes. The use of YOPRO-1, an apoptosis stain (Idziorek et al. (1995) *J. Immunol. Methods* 185:249-258), on these same parasites in the presence of Sirtinol shows that the level of expression of the LiSIR2 protein is directly proportional to the percentage of apoptosis observed in the parasites (FIG. 5B).

Example 2

Reduced Virulence of the Mutant Parasites in vitro

Figure 6A:
FIGS. 6A and 6B

The virulence of several clones having lost an allele of the LiSIR2 gene was determined in vitro by comparing the level of incorporation of Uracile $^3$H between macrophages infected with wild-type parasites and infected with the mutant strains. The infection of the macrophages derived from the THP1 line with amastigotes was routinely carried out as described previously (Sereno et al. (1998) *Antimicrob. Agents Chemother.* 42:3097-3102). In all the LiSIR2/LiSIR2::NEO clones analyzed a significant reduction of approximately 50% of the level of incorporation compared with the wild-type parasites (FIG. 6A) is observed.

Example 3

Reduced Virulence of the Mutant Parasites in vivo

The virulence of these parasites was also determined in vivo by measuring the parasitic charge in the spleens of BALB/c mice infected either with the wild-type (WT) *L. infantum* clone or with a clone without a copy of the LiSIR2 (LiSIR2+/−) gene.

Male mice aged 7 weeks (Harlan Iberica, Spain) were infected by intraperitoneal (i. p) route with $10^8$ promastigotes of the mutant clone in which a copy of the LiSIR2 gene was inactivated (LiSIR2+/−), as a control, mice of the same age and sex were infected by intraperitoneal (i. p) route with $10^8$ promastigotes of the wild-type clone. The spleens removed from the two groups of mice were homogenized and subjected to a series dilution (1 to $4.10^{-6}$) in 96-well microtitration plates. After incubation for 15 days at 26° C. the presence or absence of promastigotes in the culture wells was recorded. The titre is the last dilution which makes it possible to document one parasite/per well. The number of parasites per gram of tissue (parasitic charge) is calculated as follows:

Parasitic charge=(geometric mean of the inverse of the titre of each well in triplicate/the weight of the spleen homogenate)×the inverse of the fraction of the spleen homogenate inoculated in the first well of the culture plate.

Figure 6B:
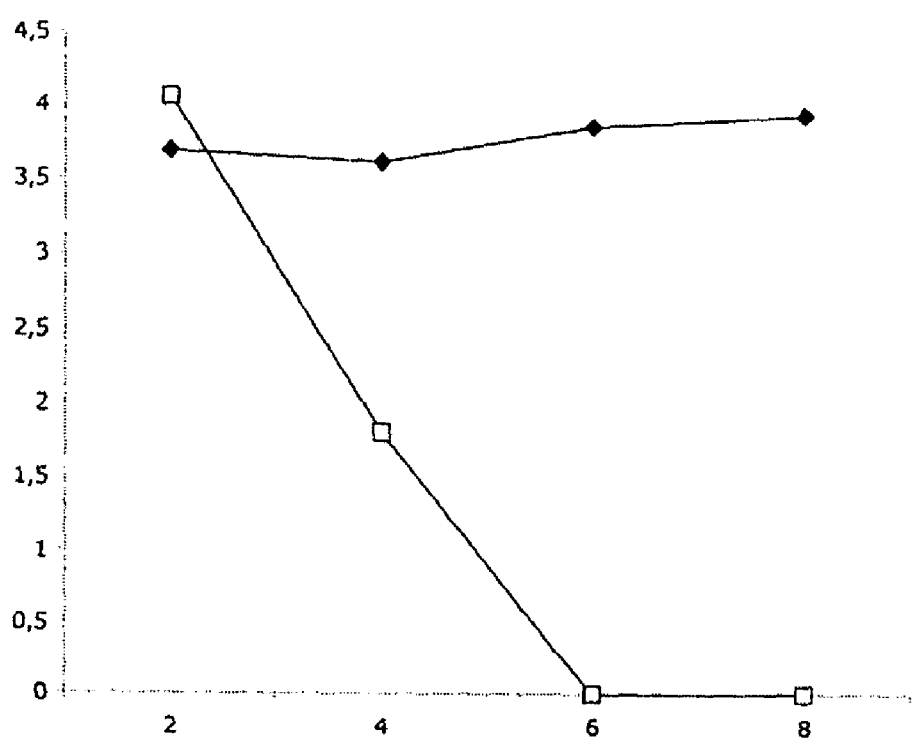

Although the LiSIR2+/− clones are infectious (parasitic charge approximately identical in both cases after two weeks of infection), a progressive reduction in the parasitic charge is observed in the mice infected with the mutant clones and no live parasite could be detected 6 weeks after infection (FIG. 6B), which means that these clones are strains particularly suitable for the preparation of a reduced live vaccine.

Example 4

Vaccination of Mice with the Mutant Parasites

The LiSIR2+/− clones were used in order to carry out vaccination trials on BALB/c mice.

A group of male mice aged 7 weeks (Harlan Iberica, Spain) (n=3) were infected by intraperitoneal route with $10^8$ promastigotes of the mutant clone, in which a copy of the gene LiSIR2 was inactivated (LiSIR2+/−). As a control, another group of mice (n=4) of the same age and sex were infected with $10^8$ promastigotes of the wild-type clone.

At the end of 6 weeks, the animals in each group received a test infection of $10^8$ promastigotes of the wild-type clone.

Then, 6 weeks later, the parasitic charge was measured as described in Example 3.

The results obtained (FIG. 7) indicate that the average parasitic charge is approximately 20,000 parasites per gram of tissue for the group of mice having received an injection of the LiSIR2+/− clone and approximately 440,000,000 parasites per gram of tissue for the other group. This confirms the vaccinating potential of the LiSIR2+/− strains of the invention.

Moreover, the protective effect induced by inactivated LiSIR2+/− parasites, i.e. killed by glutaraldehyde is also studied.

Finally, vaccination experiments similar to those described above, involving a larger number of mice (n=12) are also carried out either with the mutated clones, or with the inactivated mutated clones, in order to measure different parameters after infection, such as the parasitic charge, the production of anti-parasitic antibodies (class and sub-class), the levels of cell proliferation, as well as the cytokine secretion profile.

The invention claimed is:

1. A protozoan strain of the species *Leishmania* infantum the virulence of which is lower than that of the corresponding wild-type strain, wherein one copy of the SIR2 gene present in the genome of said strain is inactivated by insertion of the NEO gene in the sequence represented by SEQ ID NO: 3.

2. An immunogenic composition comprising the protozoan strain according to claim 1.

* * * * *